US00PP12806P2

(12) United States Plant Patent
Oliveira né e Wilhelmsen et al.

(10) Patent No.: US PP12,806 P2
(45) Date of Patent: Jul. 30, 2002

(54) AUSTRIAN PINE TREE NAMED 'TEARDROP'

(75) Inventors: Ammie Oliveira née Wilhelmsen, Salem; David Sather, Canby, both of OR (US)

(73) Assignee: Serendipity Nursery, Inc., Canby, OR (US)

( * ) Notice: Subject to any disclaimer, the term of this patent is extended or adjusted under 35 U.S.C. 154(b) by 0 days.

(21) Appl. No.: 09/649,902

(22) Filed: Aug. 28, 2000

(51) Int. Cl.[7] ..... A01H 7/00
(52) U.S. Cl. ..... Plt./213
(58) Field of Search ..... Plt./213

*Primary Examiner*—Bruce R. Campell
*Assistant Examiner*—June Hwu
(74) *Attorney, Agent, or Firm*—Klarquist Sparkman LLP

(57) ABSTRACT

A distinctly attractive pine tree in the *Pinus nigra* Family (common name known as Austrian Pine) with a dwarf, narrow, conic to columnar appearance, having dense branching, which forms a tall, slow growing, narrow specimen that can be planted at high density for effect and landscaping.

5 Drawing Sheets

The present invention relates to a new and distinct variety of Austrian Pine (*Pinus nigra*) named 'Teardrop,' which was discovered by Amie Wilhelmsen at a nursery located in Aurora, Oreg. The original plant was a seedling, which came from a group of seedlings potted in five-gallon containers for the purpose of growing *Pinus nigra*.

The 'Teardrop' variety differs from other seedlings of *Pinus nigra* in that the 'Teardrop' variety has a columnar and dwarf growth habit. More specifically the 'Teardrop' variety growth habit is characterized, in part, by the following:

(1) The narrow conic to columnar habit of this new variety is formed by the branches, which grow sharply upward forming a very acute angle with the trunk. The branch growth creates a very narrow compact crown in relation to tree height. The maximum crown spread is typically from about 30 inches to about 42 inches on 12–13 year old specimen with a height of about 8 to 10 feet.

(2) The dwarf nature of the 'Teardrop' variety is formed with annual whorl spacing from about 6 inches to about 12 inches, and new growth each year is approximately the same. Other varieties of *Pinus nigra* typically have whorl spacing from about 12 inches to about 24 inches. The crown on a typical 5-foot tall 'Teardrop', variety of tree is from about 18 inches to about 24 inches.

(3) The branches are typically smaller in size as compared to other known members of the genus, however, they have the same needle pattern as other members of the genus. Lateral branches are less susceptible to shearing caused by forces of nature than the parent species. Branches do not seem to reflect away from the trunk due to advancing growth. The expected height of a typical 'Teardrop' variety of tree at 25 years is about 20 feet to about 25 feet tall. A 12-year old specimen is presently approximately 9 feet tall with a width of 3 feet.

Asexual reproduction of this new variety by grafting, as performed at the direction of David Sather at Serendipity Nursery, Canby, Oreg., shows that the foregoing and all other characteristics and distinctions come true to form and are established and transmitted through succeeding propagations. Moreover, the tree enhibits good union between the root stock and the grafting stock with no rejection tendencies.

The accompanying FIGS. show typical specimens of the vegetative growth of this new variety, depicted in color as nearly true as it is reasonably possible to make the same in a color illustration of this character.

The following is a detailed description of the invention based on plants grown in a nursery in Canby, Oreg. Color descriptions and other terminology are used herein in accordance with ordinary dictionary significance unless otherwise noted with reference to The Royal Horticultural Society Colour Chart (R.H.S.). It should be noted that growth and/or color varies with time of year, lighting conditions, and soil and nutrient conditions. For example, leaf colors may be brighter green if the trees are grown in soil with greater nitrogen concentrations, and may be more yellow when grown in soil containing lesser amounts of nitrogen.

DETAILED DESCRIPTION

Figure 1:
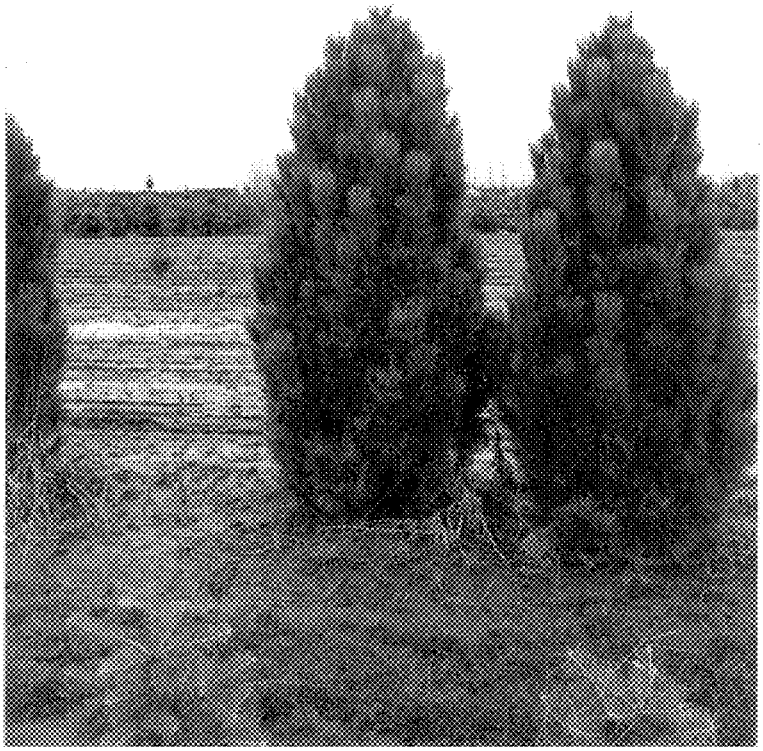
FIG. 1 depicts the basic shape of the 'Teardrop' variety (two specimens shown) at approximately 8–10 feet in height and a width of from about 30 inches to about 42 inches. The trees depicted are 12–13 years old.
Figure 2:
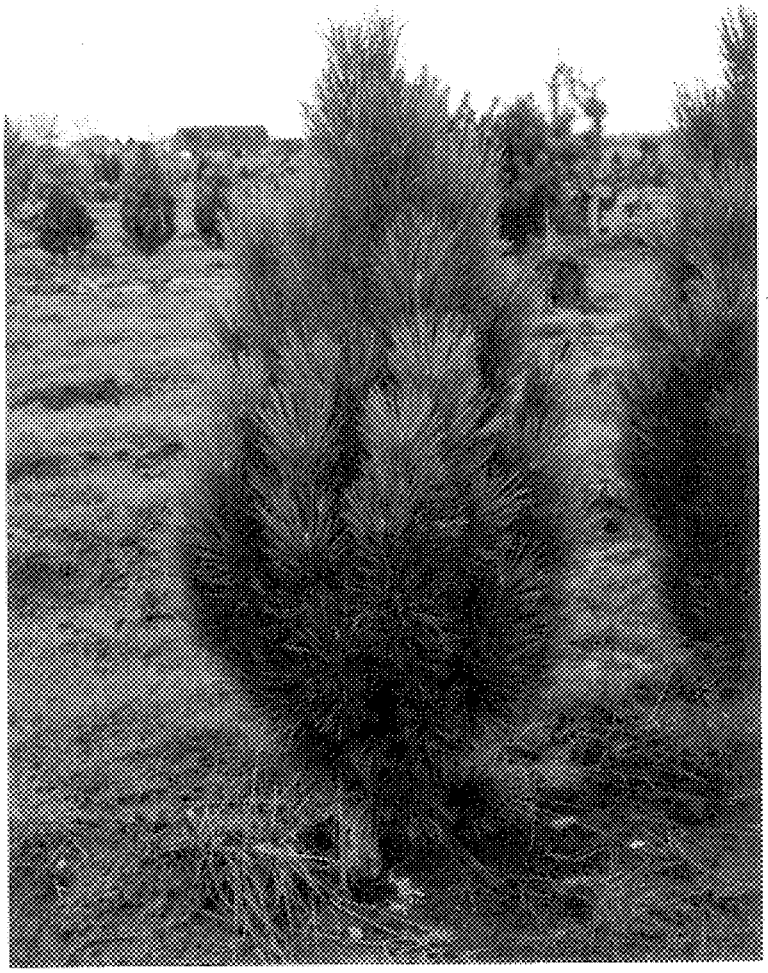
FIG. 2 depicts the basic shape of the 'Teardrop' variety. The tree is approximately 5 feet in height and has a width of 2 feet.
Figure 3:
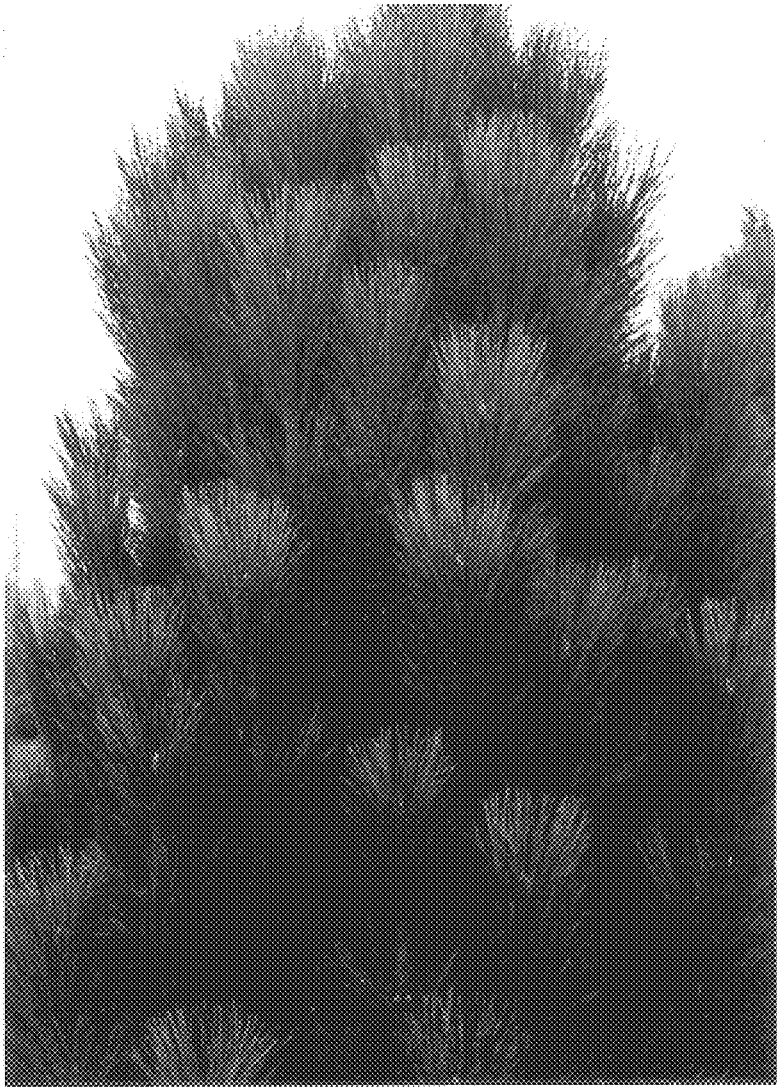
FIG. 3 depicts a close-up view of the 'Teardrop' variety, showing in greater detail the needles and branches.
Figure 4:
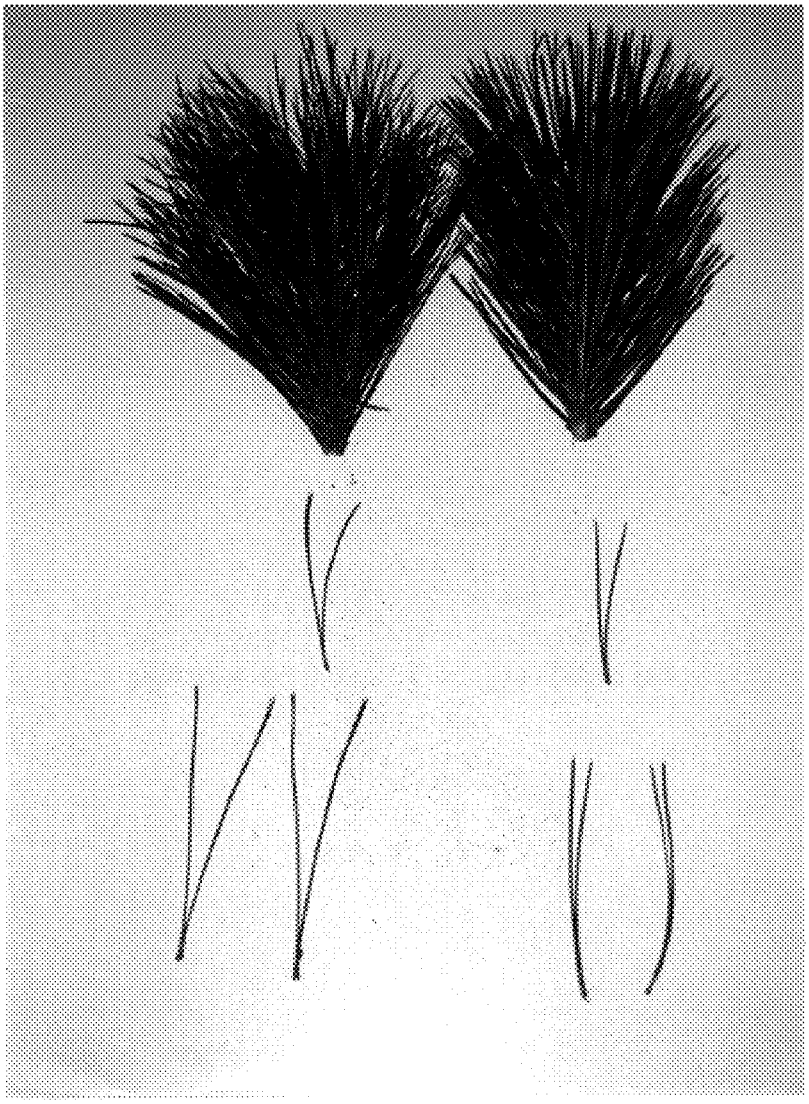
FIG. 4 depicts the difference in needles of the 'Teardrop' variety (left) and another variety of *Pinus nigra* (plant of the species, no cultivar name, non-patented).
Figure 5:
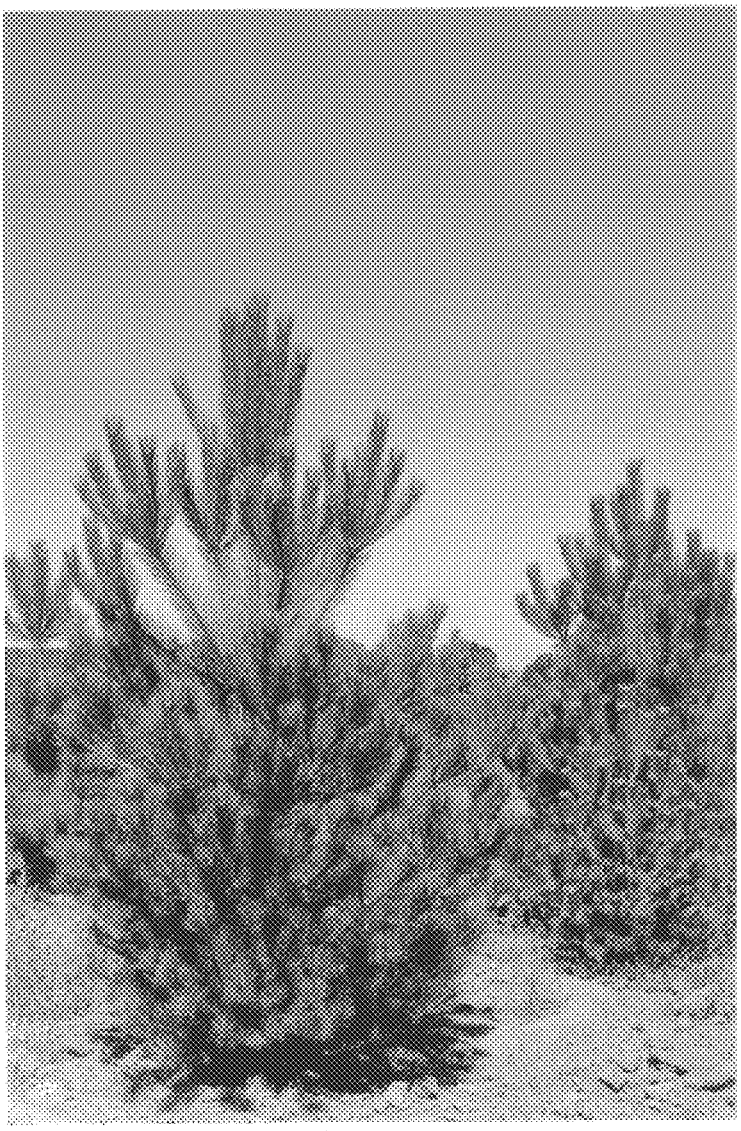
FIG. 5 depicts a *Pinus nigra* plant (plant of the species, no cultivar name, non-patented, not of the 'Teardrop' variety) for comparison. The height of the tree is between 9 feet and 11 feet, the width of the tree is between 5 feet and 6 feet, and the tree is between 5 and 6 years old.

The following is a detailed botanical description of the new 'Teardrop' variety:

Type: Austrian pine tree for landscaping.
Family: Pinaceae.
Genus: Pinus.
Species: *nigra*.

Commercial: Nigra pine, with the varietal name 'Teardrop'.

Propagation: Holds its distinguishing characteristics through succeeding propagations by asexual reproduction, specifically by grafting.

Growth habit: Branches are formed with slow growth at exceedingly narrow, acute angles relative to the trunk, resulting in a tree with a narrow, dwarf, conic figure. Branches are strongly ascending and maintain their position with increasing age. The canopy is much narrower and more dense than that of a tree typical of the species.

Vigor: The growth rate of this tree is less than the species, and is exemplified by growth of about 6 to about 12 inches of terminal growth per year. A typical twelve year old specimen is about 9 feet in height.

Needles: The needles of this tree are approximately 0.5 inches longer than other observed members of the species. The needles are also slightly thinner and therefore more flexible than needles from other observed members of the species.

Upper surface color RHS 137C graduating to RHS 138B from fascicle base to needle tip.

Lower surface color RHS 138B graduating to RHS 138C from fascicle base to needle tip.

The needle length of *Pinus nigra* 'Teardrop' is typically about 4–4.25 inches including sheath. The length of the sheath is typically about 0.25–0.33 inches. Both are longer than the common species form of *Pinus nigra* (unpatented) which has an about 3.5 inches overall needle length and a sheath length of about 0.15–0.25 inches. *Pinus nigra* 'Teardrop' has double needles joined at the sheath and a concave needle shape. The needle margins are smooth and are typically persistent up to about 10 months. The common species form of *Pinus nigra* also has double needles joined at the sheath with a concave needle shape. The needle margins of the common species observed as of this time are also smooth but the needles are typically only persistent for a period of 8 months. The apex of the needles of *Pinus nigra* 'Teardrop' is pointed, needle-like.

Branches:

*Angle.*—The branches of the 'Teardrop' variety are whorled, strongly ascending, and form an angle (measured from the horizontal) of from about 50 degrees to about 75 degrees. The angle (measured from the horizontal) of other known *Pinus nigra* specimens ranges from about 10 to about 35 degrees. The angle of the 'Teardrop' variety causes a compact growth habit against the trunk, and creates a slender crown.

*Size.*—Other specimens of *Pincus nigra* have branch sizes ranging from about 12 inches to about 24 inches in length and the new branches are from about 0.5 to about 0.75 inches in diameter. The 'Teardrop' variety displays branches from about 6 to about 12 inches in length and new branches are from about 0.75 to about 1.0 inch in diameter.

Bark: The surface texture of the bark varies by age. Immature bark is smooth and typically only broken by the shape of the lenticels and foliage abscission scars. Mature bark is rough and scaly.

*Mature bark color.*—RHS N 200C.

*Immature bark color.*—RHS N 200B.

Bud: The shape of the apical bud of the new tree is narrowly conical with the secondary buds somewhat elliptical. The secondary buds typically surround the apical bud in concentric whorls. The apical bud is typically about 1.0 inches in length with the secondary buds typically ranging from about 0.5–0.75 inches in length. The surface texture of all buds is smooth and somewhat glabrous. The buds are smaller than the common species form of *Pinus nigra*. The typical color of apical buds is RHS 155D and a typical color of secondary buds is RHS 176D.

Seeds and cones: None observed to date.

Disease and pest resistance: Not observed to be any different than common *Pinus nigra* trees growing in the area.

Hardiness: Not determined. Observations are of trees growing in the Willamette Valley of Oregon; hardiness zone 5a per USDA hardiness Zone. A few trees have also been growing in Wisconsin and have not suffered any adverse affects from two Wisconsin winter seasons.

What is claimed is:

1. A new and distinct variety of *Pinus nirga* of the 'Teardrop' variety, substantially as herein shown and described, characterized particularly by slow growth and by its strongly ascending whorled branches, forming acute angles with the trunk.

* * * * *

UNITED STATES PATENT AND TRADEMARK OFFICE

CERTIFICATE OF CORRECTION

PATENT NO. : PP 12,806 P2
DATED : July 30, 2002
INVENTOR(S) : Wilhelmsen et al.

It is certified that error appears in the above-identified patent and that said Letters Patent is hereby corrected as shown below:

Column 1,
Line 40, change the word "enhibits" to -- exhibits --

Column 4,
Line 1, change the word "*nirga*" to read -- *nigra* --
Line 6, change the word "Pincus" to -- Pinus --

Signed and Sealed this

Fifth Day of August, 2003

JAMES E. ROGAN
*Director of the United States Patent and Trademark Office*